United States Patent [19]

Ribble et al.

[11] Patent Number: 5,429,788
[45] Date of Patent: Jul. 4, 1995

[54] APPARATUS AND METHOD FOR DEPOSITING PARTICULATE MATERIAL IN A COMPOSITE SUBSTRATE

[75] Inventors: Brendon F. Ribble, Menasha; David J. Arteman, Appleton; Lyle T. Lamers, Appleton; David J. Van Eperen, Appleton; Thomas W. Van Eperen, Kaukauna, all of Wis.

[73] Assignee: Kimberly-Clark Corporation, Neenah, Wis.

[21] Appl. No.: 218,953

[22] Filed: Mar. 28, 1994

[51] Int. Cl.⁶ ............................................. B27N 3/02
[52] U.S. Cl. ........................... 264/510; 264/518; 264/113; 425/81.1; 425/83.1
[58] Field of Search ................... 264/518, 113, 510; 425/81.1, 82.1, 83.1

[56] References Cited

U.S. PATENT DOCUMENTS

| | | | |
|---|---|---|---|
| 4,715,918 | 12/1987 | Lang | 156/273.1 |
| 4,927,582 | 5/1990 | Bryson | 264/113 |
| 4,994,053 | 2/1991 | Lang | 604/367 |
| 5,017,324 | 5/1991 | Kaiser et al. | 264/510 |
| 5,028,224 | 7/1991 | Pieper et al. | 425/80.1 |
| 5,030,314 | 7/1991 | Lang | 156/390 |
| 5,056,462 | 10/1991 | Perkins et al. | 118/683 |
| 5,064,484 | 11/1991 | Craig et al. | 156/62.6 |
| 5,072,687 | 12/1991 | Mitchell et al. | 118/37 |
| 5,102,585 | 4/1992 | Pieper et al. | 264/37 |
| 5,118,376 | 6/1992 | Pigneul | 156/219 |
| 5,143,680 | 9/1992 | Molnar et al. | 264/511 |
| 5,145,351 | 9/1992 | Rossi | 425/80.1 |
| 5,151,301 | 9/1992 | Kruger et al. | 427/294 |
| 5,156,902 | 10/1992 | Pieper et al. | 428/206 |
| 5,213,817 | 5/1993 | Pelley | 425/81.1 |
| 5,227,107 | 7/1993 | Dickenson et al. | 264/113 |

FOREIGN PATENT DOCUMENTS

| | | |
|---|---|---|
| 21500338 | 6/1985 | United Kingdom . |
| 2191515A | 12/1987 | United Kingdom . |
| WO88/04165 | 6/1988 | WIPO . |

*Primary Examiner*—Mary Lynn Theisen
*Attorney, Agent, or Firm*—Jeffrey B. Curtin

[57] ABSTRACT

An apparatus and method for forming a discrete layer of particulate material within a composite fibrous web includes a first forming chamber and a supplying mechanism for providing a flow of a selected fibrous material into the first forming chamber. A second forming chamber is selectively located within the first forming chamber to selectively divide the flow of fibrous material. A conveying mechanism transports a particulate material into the second forming chamber. A depositing mechanism is located within the second forming chamber to selectively dispense the particulate material. A foraminous forming layer is movably disposed within the first forming chamber and receives the fibrous material and the particulate material. As the foraminous forming layer moves, a first fibrous layer is formed on the foraminous forming layer, the particulate material is selectively deposited on the first fibrous layer, and a second fibrous layer is formed on the particulate material thereby providing the discrete layer of particulate material within the composite fibrous web. The depositing mechanism can be configured to dispense the particulate material in a selected pattern. The depositing mechanism can also be configured to intermittently dispense the particulate material at spaced apart locations along a length of the composite fibrous web.

27 Claims, 10 Drawing Sheets

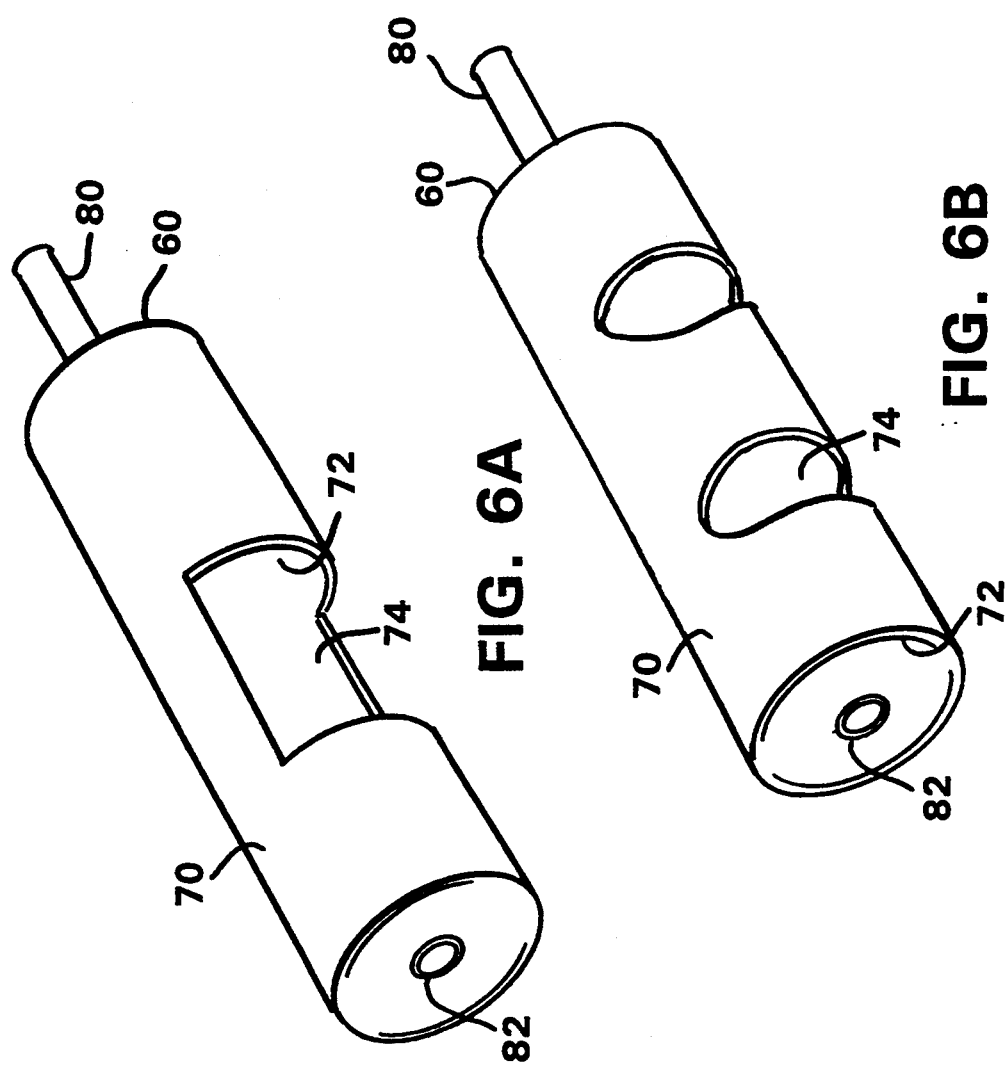

APPARATUS AND METHOD FOR DEPOSITING PARTICULATE MATERIAL IN A COMPOSITE SUBSTRATE

BACKGROUND OF THE INVENTION

1. Field of the Invention

The present invention relates to an apparatus and method for forming a layer of particulate material within a fibrous web. More particularly, the present invention relates to an apparatus and method for forming a discrete layer of high absorbency particles within an absorbent pad composed of hydrophilic fibers.

2. Description of the Related Art

Absorbent articles, such as disposable infant diapers, feminine care products, incontinence garments and the like, have included high-absorbency particles in their absorbent pad to increase the absorbent capacity of the article and to reduce the bulkiness of the article. Particular absorbent article designs have concentrated high absorbency particles in selected regions of the absorbent pad. For example, U.S. Pat. No. 5,030,314 to Lang describes an apparatus which includes a roll having discrete indentations for receiving particulate material and selectively transferring the material to a web. In some conventional arrangements, the high absorbency particles, such as superabsorbent polymers, have been substantially uniformly mixed with the absorbent fibers located within the selected layers. In other arrangements, the high absorbency particles have been substantially isolated in layers, zones or pockets within the absorbent pad with the high absorbency particles being substantially unmixed with the absorbent fibers.

Various devices and processes have been employed to manufacture the absorbent articles. Air forming techniques for forming webs of hydrophilic fibers, such as woodpulp fibers, are well known in the art. In addition, it is well known that high absorbency particles, such as superabsorbent polymers, may be mixed with the hydrophilic fibers during an airlaying process to form an absorbent web. It is also well known that the high absorbency particles may be limited to a predetermined portion of the thickness of the absorbent web.

Conventional apparatus and methods for forming absorbent webs, such as those described above, have not been sufficiently satisfactory. For example, the devices may be overly complex and expensive and may not provide the capability to form patterned or intermittent, discrete layers of particulate materials. The rate and consistency of delivery of the particulate material may not be adequately controlled, and the systems may be excessively sensitive to changing variables in the process.

SUMMARY OF THE INVENTION

In response to the discussed difficulties and problems encountered in the prior art a new apparatus and method for forming a layer of particulate material within a composite fibrous web have been discovered.

In one aspect, the present invention can provide an apparatus for forming a discrete layer of particulate material within a composite fibrous web. The apparatus includes a first forming chamber and a supplying means for providing a flow of a selected fibrous material into the first forming chamber. A second forming chamber is selectively located within the first forming chamber to selectively divide the flow of the fibrous material. A conveying means transports a particulate material into the second forming chamber.

A depositing means is located within the second forming chamber and selectively dispenses the particulate material. A foraminous forming layer is movably disposed within the first forming chamber and is configured to receive the flow of fibrous material and the dispensed particulate material. The foraminous forming layer is constructed to receive a formation of a first fibrous layer, to receive said dispensed particulate material on the first fibrous layer, and to receive a second fibrous layer formed on the particulate material, thereby forming the discrete layer of particulate material within the composite fibrous web.

In another aspect of the apparatus of the invention, the depositing means includes a forming grate which has at least one grate opening therethrough. In operation, the particulate material is selectively dispensed through the grate opening in the forming grate and deposited on the first fibrous layer in a selected pattern.

In another aspect of the apparatus of the invention, the depositing means includes a rotatable drum which has an interior chamber therein and at least one drum opening therethrough. In operation, the particulate material is received in the interior chamber of the rotatable drum and intermittently dispensed through the drum opening as the rotatable drum rotates such that the particulate material is intermittently deposited on the first fibrous layer at spaced apart locations along a length of the composite fibrous web.

In another aspect, the present invention can provide a method for forming a patterned, discrete layer of particulate material within a composite fibrous web. A flow of a selected fibrous material is provided into a first forming chamber. A flow of a particulate material is provided into a second forming chamber which is selectively located within the first forming chamber. The second forming chamber selectively divides the flow of the fibrous material within the first forming chamber. The fibrous material and particulate material are deposited on a moving, foraminous forming layer which is located within the first forming chamber. As the foraminous forming layer moves, a first fibrous layer is formed on the foraminous forming layer. The particulate material is deposited on the first fibrous layer in a selected pattern. A second fibrous layer is formed on the particulate material thereby forming the patterned, discrete layer of particulate material within the composite fibrous web.

A further aspect of the invention can provide a method for forming an intermittent, discrete layer of particulate material within a composite fibrous web. A flow of a selected fibrous material is provided into a first forming chamber. A flow of a particulate material is provided into a second forming chamber which is selectively located within the first forming chamber. The second forming chamber selectively divides the flow of the fibrous material within the first forming chamber into a first portion and a second portion. The first portion of the fibrous material is deposited on a moving, foraminous forming layer located within the first forming chamber to provide a first fibrous layer. The particulate material is intermittently deposited on the first fibrous layer. The second portion of the fibrous material is deposited on the particulate material to provide a second fibrous layer thereby forming the intermittent, discrete layer of particulate material within the composite fibrous web. In a particular aspect of the invention, the particulate material may be intermittently deposited by a rotating drum which has an interior chamber therein and at least one drum opening therethrough. The drum receives the particulate material in the interior chamber and selectively dispenses the particulate material through the drum opening as the drum rotates such that the particulate material is intermittently deposited at spaced apart locations along a length of the composite fibrous web.

The present invention, in its various aspects, can advantageously provide an apparatus and method which, when compared to conventional devices, can more efficiently provide a discrete layer of particulate material within selected regions of a composite fibrous web, and can position the particulate material in a manner which is generally independent of the flow of the fibrous material used to form the web. As a result, the present invention can advantageously provide a composite fibrous web wherein particulate material can be placed at selected locations without concomitantly placing larger proportions of fibrous material at those locations. The apparatus can also have lower complexity and lower equipment costs while affording sufficient controllability to provide desired patterned or intermittent, discrete layers of particulate material within a composite fibrous web.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the appended claims.

FIGS. 6A and 6B representatively show perspective views of a rotatable drum of the present invention having an interior chamber therein and a drum opening therethrough configured in two different patterns;

DETAILED DESCRIPTION OF THE INVENTION

The following detailed description will be made in the context of forming a layer of high absorbency particles within a composite fibrous web which can be used as an absorbent core in a disposable diaper article. It should be understood, however, that the present invention may also be used to form a layer of other types of particulate material within a composite fibrous web. In addition, it should be readily understood that the composite fibrous web of the present invention may also be used as an absorbent core for other types of absorbent articles, such as, for example, training pants, feminine care products, incontinence garments and the like. All of such alternative configurations are contemplated as being within the scope of the present invention.

The invention is particularly useful for forming a layer of particles of organic or inorganic high absorbency (e.g. superabsorbent) material within a composite fibrous web. Suitable inorganic high-absorbency materials include, for example, absorbent clays and silica gels. Organic high absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly crosslinked to impart desired levels of water insolubility to the material. Crosslinking may, for example, be by irradiation or by covalent, ionic, Van der Waals, or hydrogen bonding. Suitable materials are available from various commercial vendors, such as Dow Chemical Company, Hoechst Celanese Corporation, Allied-Colloid and Stockhausen. Typically, the high absorbency material is capable of absorbing at least about 15 times its weight in water, and desirably is capable of absorbing at least about 25–50 times its weight in water.

The particles of high absorbency material may have regular shapes or irregular shapes, such as elongated forms. For example, particles of high absorbency material may be configured in the form of granules, flakes, fibers, or the like. The particles typically measure about 50–1000 micrometers in size and desirably measure about 100–800 micrometers in size.

Figure 1A:
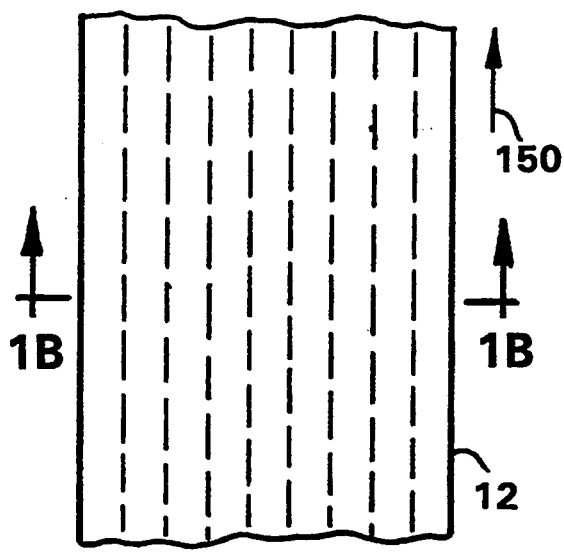
FIGS. 1A and 1B representatively illustrate a top plan view and a side elevational view, respectively, of a composite fibrous web having a patterned, discrete layer of particulate material formed by the invention.
Figure 1B:
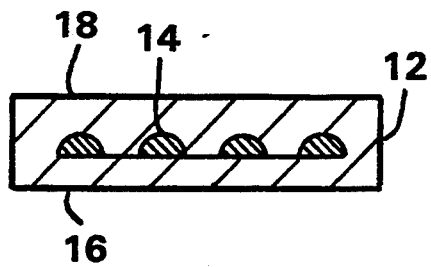

A composite fibrous web having a layer of particulate material formed by the apparatus and method of the present invention is representatively illustrated in FIGS. 1A and 1B. A similar composite fibrous web having an intermittent, discrete layer of particulate material formed by the apparatus and method of the present invention is representatively illustrated in FIGS. 1C and 1D. A composite fibrous web 12, such as a web comprising woodpulp fluff fibers, includes a layer of particulate material 14, such as, for example, particles of high absorbency material. Desirably, the layer of particulate material 14 is formed between a first fibrous layer 16 and a second fibrous layer 18. The layer of particulate material 14 may be patterned, as representatively illustrated in FIGS. 1A and 1B, and intermittent or spaced apart, as representatively illustrated in FIGS. 1C and 1D.

Figure 1C:
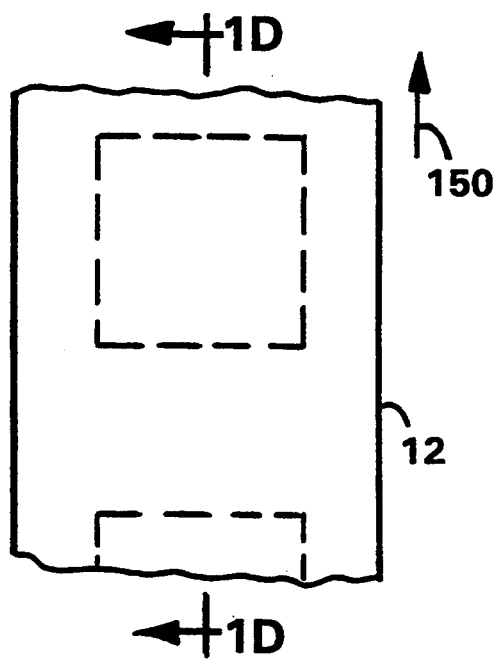
FIGS. 1C and 1D representatively show a top plan view and a side elevational view, respectively, of a composite fibrous web having an intermittent, discrete layer of particulate material formed by the invention.
Figure 1D:
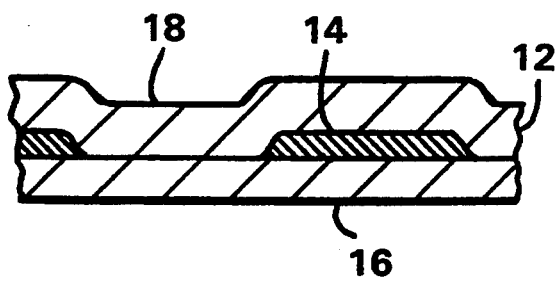
Figure 2:
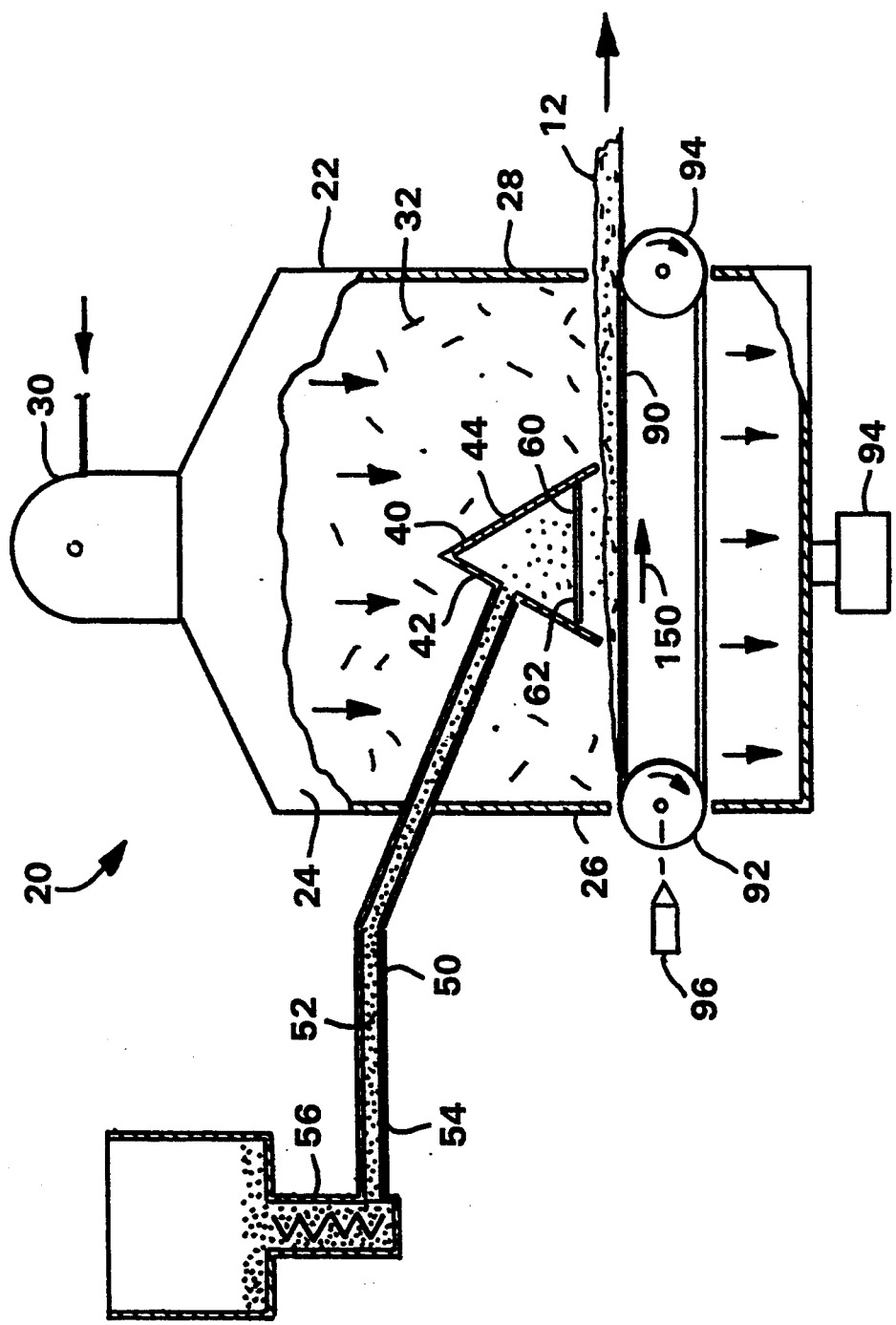
FIG. 2 representatively shows a side elevational view of one embodiment of an apparatus of the present invention for forming a patterned, discrete layer of particulate material within a composite fibrous web.

With reference to FIG. 2, a representative apparatus and method of the invention is configured to form a layer of particulate material within a composite fibrous web. The apparatus 20 includes a first forming chamber 22 and a supplying means 30, such as a fiberizer hammermill, which provides a flow of fibrous material 32 into the first forming chamber 22. A second forming chamber 40 is located within the first forming chamber 22. The second forming chamber 40 selectively divides the flow of the fibrous material 32 within the first forming chamber 22. A conveying means 50, such as a suitable pipe conduit, transports a particulate material 52, such as particles of high absorbency material, into the second forming chamber 40. A depositing means 60, which is located within the second forming chamber 40, selectively dispenses the particulate material 52. A foraminous forming layer 90, which is movably disposed within the first forming chamber 22, is configured to receive the flow of fibrous material 32 and the dispensing of particulate material 52 thereon. As the foraminous forming layer 90 moves in a machine direction 150, the flow of fibrous material 32 is selectively divided by the second forming chamber 40 such that a first fibrous layer 16 (FIG. 1A–1D) is formed on the foraminous forming layer 90. Alternatively, a tissue layer may be provided on the foraminous forming layer 90 such that the first fibrous layer 16 is formed on the tissue layer. The particulate material 52 is deposited on the first fibrous layer 16 and a second fibrous layer 18 is formed on the particulate material 52 thereby forming a layer of particulate material 14 (FIGS. 1A–1D) within a composite fibrous web 12.

As representatively illustrated in FIG. 2, the first forming chamber 22 includes side walls 24 and end walls 26 and 28 which are constructed and arranged to define a generally enclosed volume. The end walls 26 and 28 have suitable entrance and exit openings formed therethrough to allow the entry of the foraminous forming layer 90 and the removal of the composite fibrous web 12 from the first forming chamber 22. The side walls 24 and end walls 26 and 28 may be connected together by any means known to those skilled in the art. For example, the walls may be welded, mechanically fastened using screws, bolts, staples and the like or adhesively fastened together. The side walls 24 and end walls 26 and 28 can be made from any material which can provide a generally sealed, enclosed volume. For example, the side walls 24 and end walls 26 and 28 can be made from steel, aluminum, or a polycarbonate such as Lexan® which is manufactured by the General Electric Company.

The supplying means 30 may comprise any one of a number of types of conventional devices for providing a flow of fibrous material. Examples of such a device include fiberizing mechanisms. For example, sheets of fibrous material may be fed into a fiberizing mechanism and disintegrated into a fibrous material 32. The fibrous material 32, which includes a plurality of individual fibers, is injected, or otherwise introduced, into the first forming chamber 22. Typically, the fibrous material 32 is composed of absorbent, woodpulp fibers commonly referred to as fluff. The fibrous material 32 may also be composed of staple fibers, polymeric fibers, cellulosic fibers and mixtures thereof, as well as mixtures of absorbent fibers with generally hydrophobic fibers. The fibrous material 32 may optionally be treated to impart desired levels of hydrophilicity, employing techniques well known in the art.

As representatively illustrated in FIG. 2, the second forming chamber 40 is selectively located within the first forming chamber 22 to divide the flow of fibrous material 32. The second forming chamber 40 includes a pair of end walls 42 and 44 which are connected to the side walls 24 of the first forming chamber 22 and to each other to define a generally enclosed volume. Desirably, the end walls 42 and 44 of the second forming chamber 40 are arranged to slant toward each other and intersect to form a tepee configuration, as representatively illustrated in FIG. 2, to effectively divide the flow of fibrous material 32 in the first forming chamber 22 into a first portion and a second portion. The second forming chamber 40 also isolates the particulate material 52 from the flow of fibrous material 32. Thus, the particulate material 52 does not intermix with the flow of fibrous material 32. Alternatively, the second forming chamber 40 may be configured in any shape or size which provides the desired composite fibrous web 12. The end walls 42 and 44 of the second forming chamber 40 have suitable entrance and exit openings formed therethrough to allow the entry and removal of the partially formed composite fibrous web 12. The end walls 42 and 44 of the second forming chamber 40 may be connected to the side walls 24 of the first forming chamber 22 and to each other by any means known to those skilled in the art. For example, the end walls may be welded, mechanically fastened using screws, bolts, staples and the like or adhesively fastened to the side walls 24 of the first forming chamber 22. The end walls 42 and 44 of the second forming chamber 40 may be made from any suitable material such as, for example, a polycarbonate under the tradename Lexan®.

Figure 4:
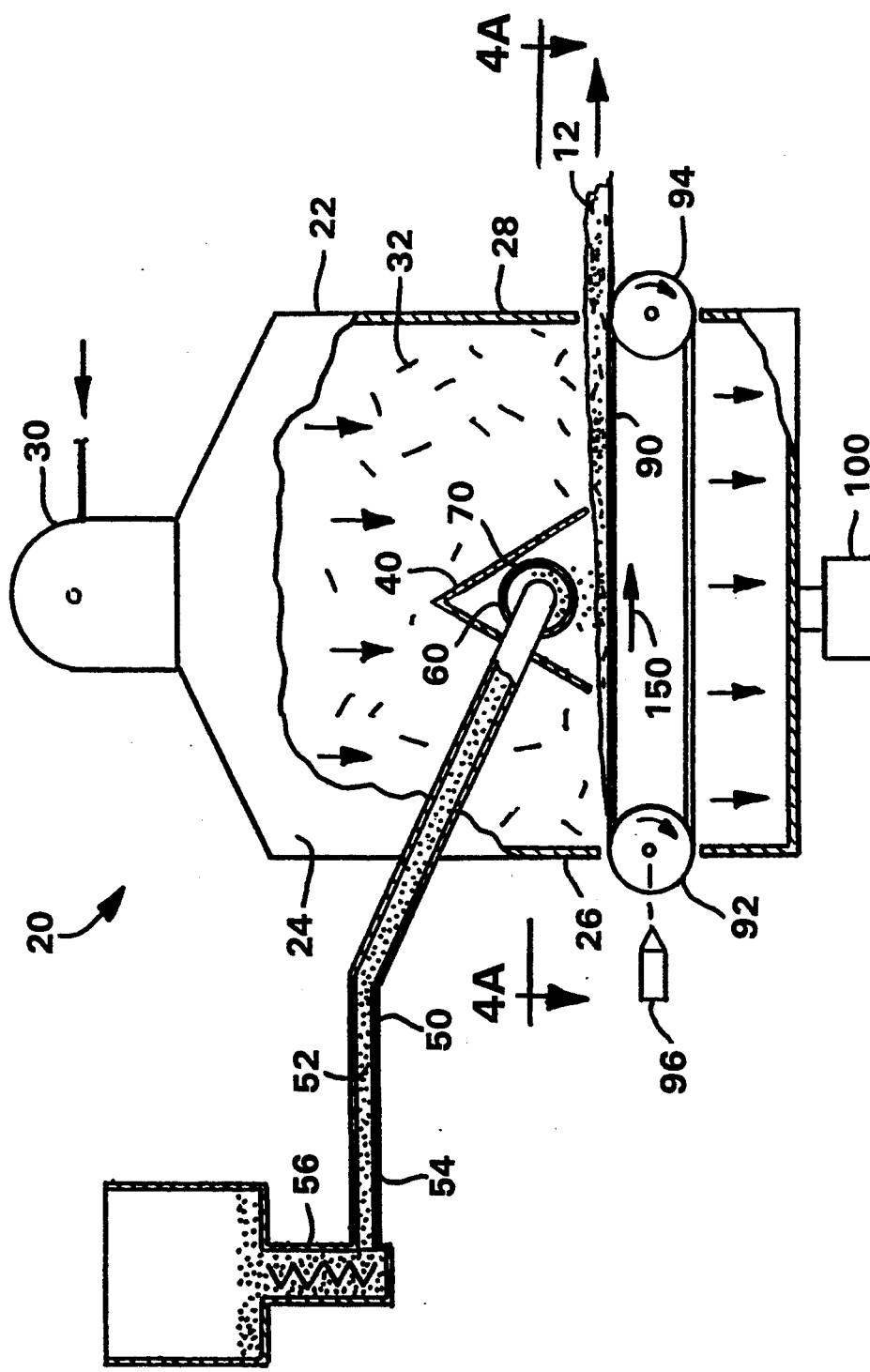
FIG. 4 representatively shows a side elevational view of an embodiment of an apparatus of the present invention for forming an intermittent, discrete layer of particulate material within a composite fibrous web.
Figure 4A:
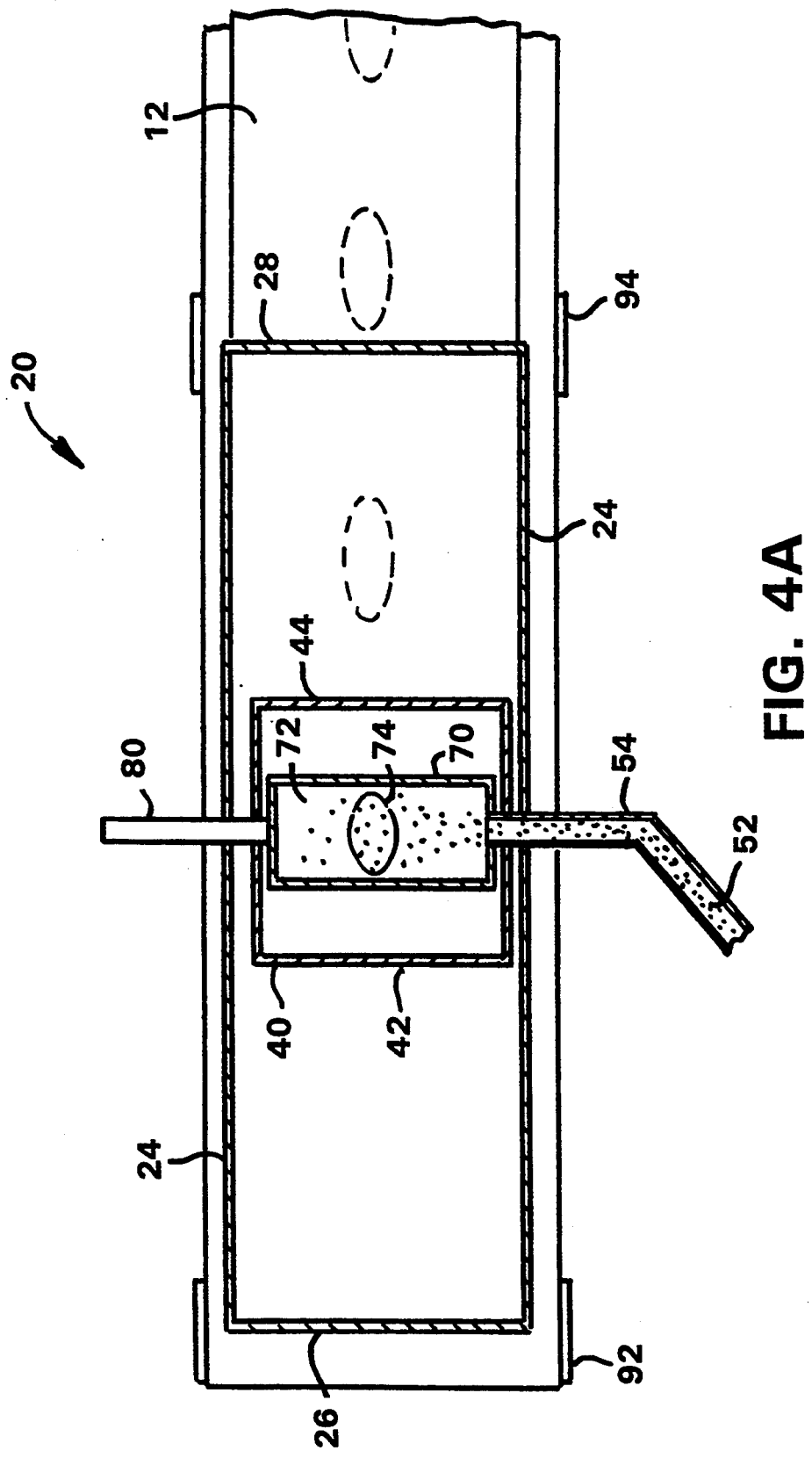
FIG. 4A representatively shows a top plan view of one example of the apparatus illustrated in FIG. 4.

Alternatively, the second forming chamber 40, as representatively illustrated in FIG. 4A, may include a pair of side walls which are connected to the end walls 42 and 44 of the second forming chamber 40 to define an enclosed volume within the first forming chamber 22. Such side walls of the second forming chamber 40 would be located and spaced inward from the side walls 24 of the first forming chamber 22. Thus, in this alternative configuration, the second forming chamber 40 would define a generally enclosed volume that is spaced apart from the side walls 24 and end walls 26 and 28 of the first forming chamber 22. Subsequently, the fibrous material 32 would only be selectively divided along a portion of the composite fibrous web 12 corresponding to the size and relative position of the second forming chamber 40 within the first forming chamber 22. For example, the fibrous material 32 would not be selectively divided by the second forming chamber 40 in the spaced apart area between the side walls of the second forming chamber 40 and the side walls 24 of the first forming chamber 22.

As representatively illustrated in FIG. 2, the apparatus and method of the present invention further includes a conveying means 50 for transporting the particulate material 52, such as high absorbency particles composed of superabsorbent hydrogel polymers, into the second forming chamber 40. The conveying means 50 may include a conveying conduit 54 for transporting the particulate material 52 into the second forming chamber 40. The particulate material 52 may flow through the conveying conduit 54 as a result of gravitational forces. Alternatively, the conveying means may include a conveying gas stream which is contained within the conveying conduit 54 and provided by a conveying blower. The particulate material 52 may be delivered into the conveying conduit 54 by any suitable method known to those skilled in the art, For example, the present invention may include a particulate regulating means 56 for providing a selected mass flow rate of the particulate material 52 into the conveying conduit 54 and into the second forming chamber 40. It should be readily understood that the amount of the particulate material 52 delivered into the second forming chamber 40 is dependent upon the desired forming rate of the composite fibrous web 12 and the weight percent of particulate material 52 desired to be contained within the composite fibrous web 12.

In the illustrated embodiment, the conveying means 50 includes a particulate regulating means 56 which is constructed and configured to provide a particulate mass flow rate which is within the range of about 20-155 gm/sec. Various types of particulate regulating means may be employed with the present invention. For example, the particulate regulating means 56 may rely on gravitational forces to provide the mass flow rate of particulate material 52 into the conveying conduit 54. Desirably, the invention employs a "weight-in loss" type of particulate regulating means such that the amount of particulate material 52 being delivered into the conveying conduit 54 can be regulated. This device can thereby help control the delivery of the desired amounts of particulate material 52 into the second forming chamber 40 and onto the composite fibrous web 12. In the illustrated embodiment, the particulate regulating means 56 is a feed screw device which relies on gravitational forces to regulate the flow of the particulate material 52 into the conveying conduit 54. Alternatively, the particulate regulating means 56 may be a LWF3-35 feeder manufactured by K-tron Corp., a company located in Pitman, N.J. Other equivalent devices may also be employed with the present invention.

If a conveying gas stream is desired, various types of commercially available blower devices may be employed with the present invention. For example, the conveying gas stream may be provided by a VB-019 blower manufactured by Spencer Turbine, a company located in Windsor, Conn. The blower may supply a conveying gas stream velocity of from about 1370 m/sec (about 4,500 ft/sec) to about 2135 m/sec (about 7,000 ft/sec). The conveying conduit 54 may then transport the particle/gas mixture composed of the particulate material 52 entrained in the conveying gas stream into the second forming chamber 40.

As representatively illustrated in FIG. 2, the conveying conduit 54 extends into the second forming chamber 40 such that the particulate material 52 is transported into the second forming chamber 40. For example, the conveying conduit 54 may extend through the end wall 26 of the first forming chamber 22 and through the end wall 42 of the second forming chamber 40. Alternatively, as representatively illustrated in FIGS. 4-5, the conveying conduit 54 may extend through a side wall 24 of the first forming chamber 22 and directly into the second forming chamber 40.

As representatively illustrated in FIG. 2, the apparatus and method of the present invention further includes a depositing means 60 which is located within the second forming chamber 40. The depositing means 60 selectively dispenses the particulate material 52. The depositing means 60 can be configured to dispense the particulate material 52 such that the amount and location of the particulate material 52 in the composite fibrous web 12 can be varied in both a machine direction and a cross machine direction and the z-direction. At any particular location along the apparatus or method, the machine direction is the direction along which the fibrous web 12 is intended to move. The cross machine direction is perpendicular to the machine direction and parallel to the plane of the fibrous web 12. The z-direction is perpendicular to the plane of the fibrous web 12. For example, in one aspect of the invention representatively illustrated in FIG. 2, the depositing means 60 may include a forming grate 62. The forming grate 62 extends in the machine direction 150 between the end walls 42 and 44 of the second forming chamber 40. The forming grate 62 may be connected to the end walls 42 and 44 of the second forming chamber 40 by any means known to those skilled in the art. For example, the forming grate 62 may be welded, mechanically fastened using screws, bolts, staples and the like or adhesively fastened to the end walls 42 and 44 of the second forming chamber 40. Desirably, the forming grate 62 is also connected by any suitable means to the side walls 24 of the first forming chamber 22. The forming grate 62 may be made from any suitable material such as, for example, a polycarbonate under the tradename Lexan ® as previously described.

Figure 3A:
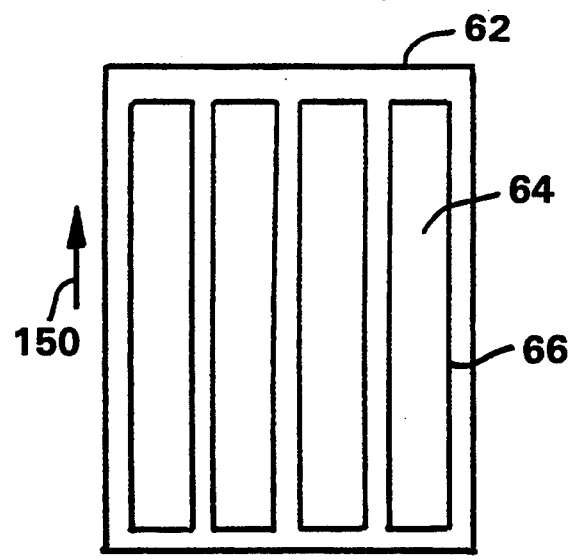
FIGS. 3A and 3B representatively show top plan views of two different embodiments of the forming grate of the present invention.
Figure 3B:
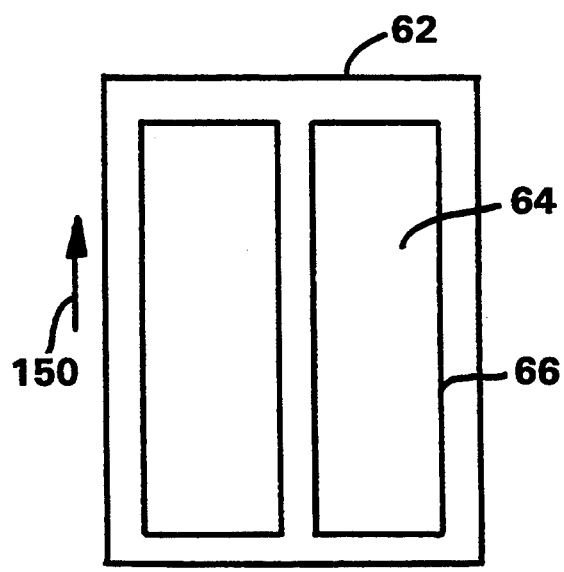

As representatively illustrated in FIGS. 3A and 3B, the forming grate 62 has at least one grate opening 64 therethrough. The grate opening 64 is configured to selectively dispense and deposit the particulate material 52 on the first fibrous layer 16 (FIGS. 1A and 1B) in a selected pattern. The quantity and size of the grate openings 64 will vary depending upon the desired configuration of the particulate material 52 within the composite fibrous web 12. For example, as representatively illustrated in FIGS. 3A and 3B, the forming grate 62 may have two or more grate openings 64 configured as channels 66 such that, in use, the particulate material 52 is deposited on the first fibrous layer 16 in discrete strips along a length of said composite fibrous web 12. An example of a composite fibrous web 12 having a discrete layer of particulate material 14 configured as discrete strips with void spaces therebetween is representatively illustrated in FIGS. 1A and 1B. Thus, in this configuration, the location of the particulate material 52 varies in the cross direction. The size of the opening 64 may also determine the thickness and z-directional placement of the particulate material 52. For example, a small opening 64 may result in a thicker layer of particulate material 14 within the composite fibrous web 12 compared to a large opening when the same amount of particulate material 52 is deposited onto the composite fibrous web 12.

Figure 5:
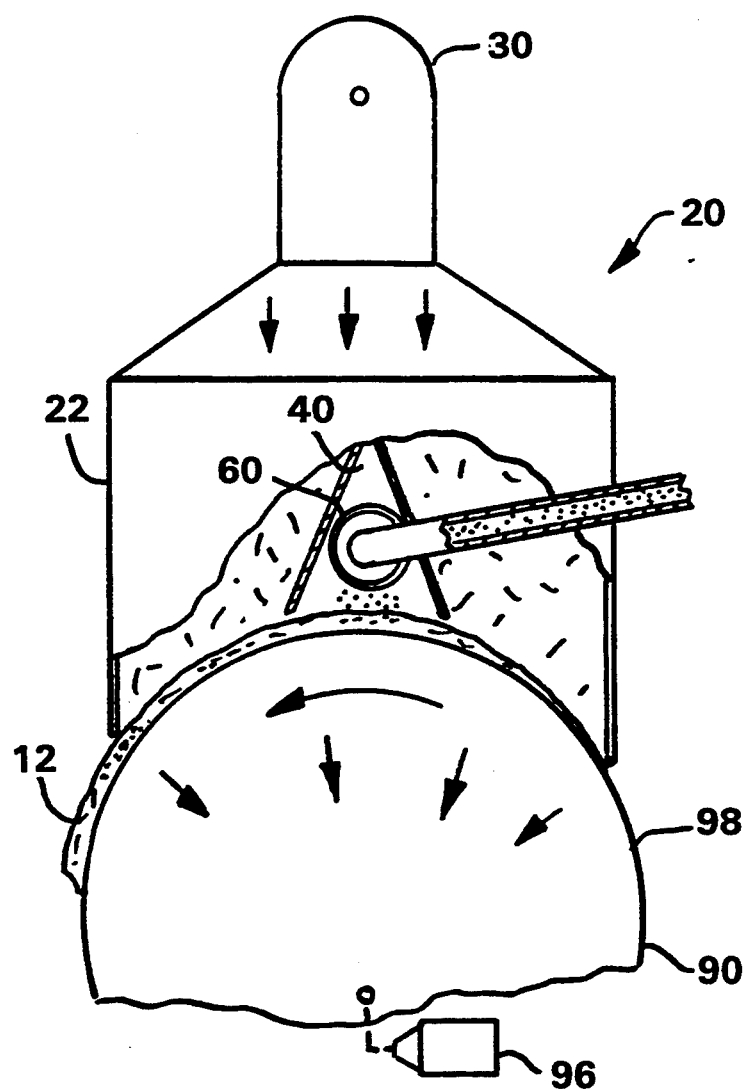
FIG. 5 representatively shows a side elevational view of another embodiment of an apparatus of the present invention for forming an intermittent, discrete layer of particulate material within a composite fibrous web.

In an alternative aspect of the invention as representatively illustrated in FIGS. 4-5, the depositing means 60 may include a rotatable drum 70. The rotatable drum 70 is located within the second forming chamber 40. FIGS. 6A and 6B provide a more detailed illustration of representative examples of the rotatable drum 70. The rotatable drum 70 includes opposed ends, an interior chamber 72 therein and at least one drum opening 74 therethrough. At least one shaft 80 is connected to an end of the rotatable drum 70. The shaft 80 may be connected to the rotatable drum 70 by any suitable means known to those skilled in the art such as, for example, welding.

The shaft 80 of the rotatable drum 70 may be rotatably connected to a side wall 24 of the first forming chamber 22 such as, for example, through the use of a suitable bearing connected to the side wall 24. Alternatively, the side wall 24 of the first forming chamber 22 may include a circular opening therethrough such that the shaft 80 of the rotatable drum 70 extends through the circular opening. The shaft 80 and rotatable drum 70 may be supported and driven by any means known to those skilled in the art. For example, the shaft 80 and rotatable drum 70 may be driven from a primary line shaft of the apparatus 20 or any of the other elements of the apparatus 20 such as the foraminous forming layer 90. Alternatively, the shaft 80 may be directly driven by an electric motor.

Desirably, the end of the rotatable drum 70 which is opposite the end having the shaft 80 connected thereto has a particle opening 82 therethrough to allow the conveying conduit 54 of the conveying means 50 to extend into the interior chamber 72 of the rotatable drum 70. For example, as representatively illustrated in FIGS. 4-5, the conveying conduit 54 of the conveying means 50 may extend through a side wall 24 of the first forming chamber 22 and through the particle opening 82 in the end of the rotatable drum 70 such that the particulate material 52 can be transported into the second forming chamber 40 and into the interior chamber 72 of the rotatable drum 70. In such a configuration, the rotatable drum 70 is supported on a cantilevered shaft with an end of the shaft being supported by a suitable bearing connected to the side wall 24 of the first forming chamber 22 or a suitable support frame.

Thus, the rotatable drum 70 is configured to receive the particulate material 52 in the interior chamber 72 and is configured to intermittently dispense the particulate material 52 through the drum opening 74 (FIGS. 6A and 6B) as the rotatable drum 70 rotates. Thus, in use, the particulate material 52 is intermittently deposited on the first fibrous layer 16 at spaced apart locations along a length of the composite fibrous web 12. An example of a composite fibrous web 12 having an intermittent layer of particulate material 14 formed by the present invention is representatively illustrated in FIGS. 1C and 1D.

Figure 7A:
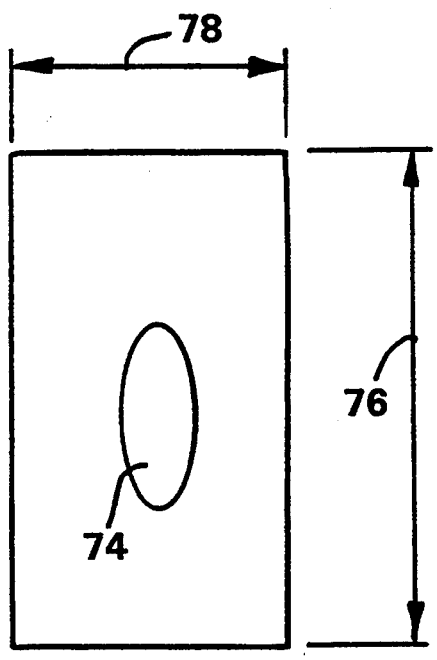
FIGS. 7A through 7D representatively show alternative configurations for the drum opening in the rotatable drum of the present invention.
Figure 7B:
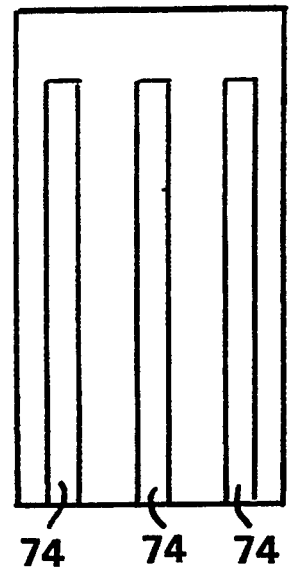
Figure 7C:
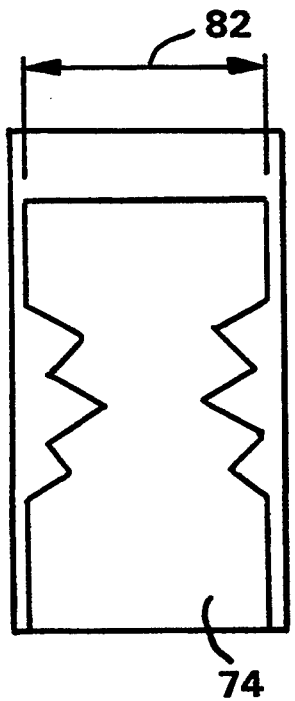
Figure 7D:
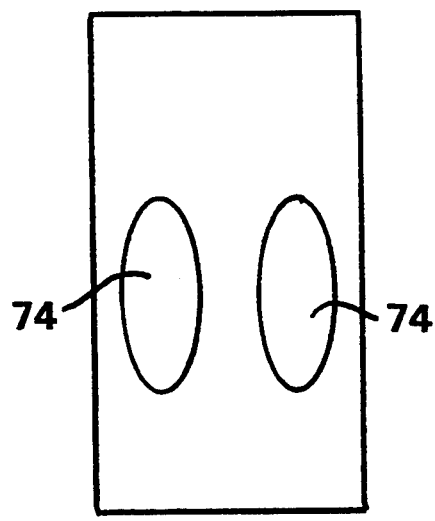

In one aspect of the invention, the drum opening 74 in the rotatable drum 70 may be configured such that the particulate material 52 which is intermittently dispensed through the drum opening 74 is deposited on the first fibrous layer 16 (FIG. 1C and 1D) in a selected pattern. The distribution of the particulate material 52 can be varied along both the machine direction 150 and the cross direction of the resulting composite fibrous web 12 and also along the z-direction or thickness of the composite fibrous web 12. As representatively illustrated in FIGS. 6A, 6B and 7A-7D, the drum opening 74 may be configured in many alternative patterns depending upon the desired configuration of the particulate material as it is deposited onto the first fibrous layer 16 (FIG. 1C and 1D). For example, the drum opening 74 in the rotatable drum 70 may be configured in an elliptical pattern. Desirably, the drum opening 74 has an opening width 82, as representatively illustrated in FIG. 7C, which is controlled such that the particulate material 52 is deposited within the center portion of the composite fibrous web 12. The center portion of the composite fibrous web 12 is located between two outer portions which desirably are substantially free of the particulate material 52. As representatively illustrated in FIG. 7A, the configuration of the drum opening 74 can vary along a circumferential length 76 and a drum width 78 of the rotatable drum 70. In addition, the rotatable drum 70 may have more than one drum opening 74 as representatively illustrated in FIGS. 6B, 7B and 7D.

As representatively illustrated in FIGS. 2 and 4-5, the different aspects of the present invention further include a foraminous forming layer 90. The foraminous forming layer 90 may comprise a foraminous forming screen configured as an endless belt which moves about a pair of support rollers 92 and 94, as representatively illustrated in FIGS. 2 and 4. A suitable driving means, such as an electric motor 96, may be operably connected to move the foraminous forming layer 90 through the first forming chamber 22 at a selected speed along the machine direction 150. The fibrous material 32 and the particulate material 52 are deposited onto the foraminous forming layer 90 to form the composite fibrous web 12, which may eventually be used as an absorbent core within an absorbent article. Since the foraminous forming layer 90 moves generally from the end wall 26 of the first forming chamber 22 toward the exit opening through the end wall 28 of the first forming chamber 22, the depth or thickness of the composite fibrous web 12 on any particular section of the foraminous forming layer 90 gradually increases as that forming layer section traverses through the first forming chamber 22. The fiber deposition rate onto the foraminous forming layer 90 and the movement speed of the foraminous forming layer can be suitably adjusted to control the finally formed thickness of the composite fibrous web 12. In addition, a tissue layer may be placed between the foraminous forming layer 90 and the first fibrous layer 16 such that the fibrous material and particulate material are deposited onto the tissue layer.

Alternatively, the foraminous forming layer 90 may comprise a foraminous forming screen configured on an outer circumferential surface of a forming drum 98, as representatively illustrated in FIG. 5. A suitable driving means, such as an electric motor 96, rotates the forming drum 98 to move the foraminous forming layer 90 through the first forming chamber 22.

The apparatus and method of the different aspects of the present invention may further include a vacuum means 100, as representatively illustrated in FIGS. 2 and 4, for drawing the fibrous material 32 and the particulate material 52 onto the foraminous forming layer 90. The vacuum means 100, such as a conventional blower mechanism, is typically located underneath the foraminous forming layer 90 to create an air flow which is generally directed from the supplying means 30, through the first forming chamber 22 and past the foraminous forming layer 90. This airflow helps to direct and control the deposition of the fibrous material 32 and particulate material 52 onto the foraminous forming layer 90.

In another aspect, the apparatus and method of the invention may include a phasing means. For example, the invention, as representatively illustrated in FIGS. 4 and 5, may further include a phasing means to properly control and sequence the rotation of the rotatable drum 70 to provide the desired placement of the intermittent layer of particulate material 14 (FIGS. 1C and 1D) within the composite fibrous web 12. The phasing means controls the rotation of the rotatable drum 70 to provide a desired registration between the intermittent layer of particulate material 14 and a selected deposition region along the machine direction 150 or length of the composite fibrous web 12.

Figure 8:
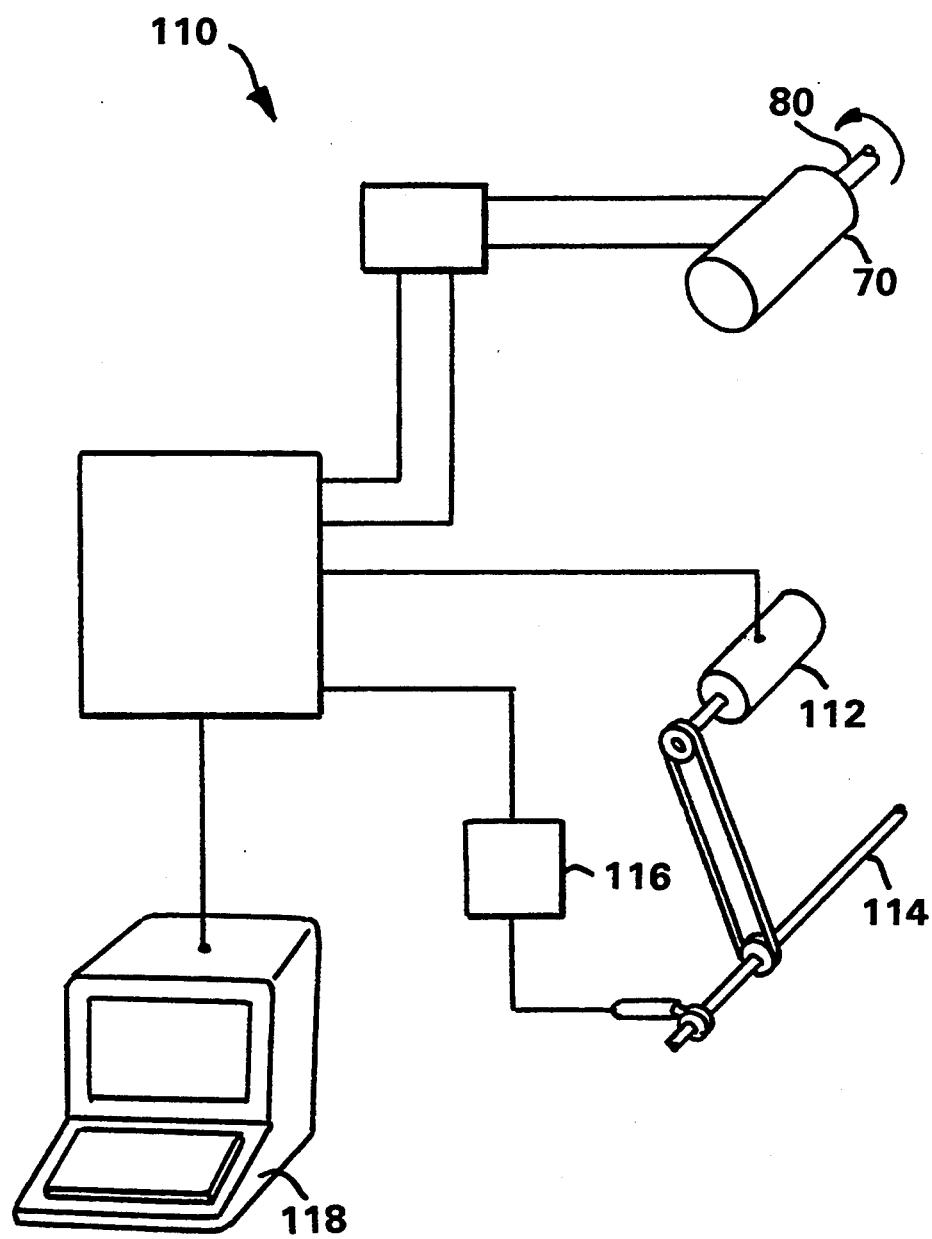
FIG. 8 shows a schematic representation of a phasing control system employed in the present invention.

A particular aspect of the invention includes the phasing means representatively shown in FIG. 8. A phasing means 110 for determining machine position and timing can, for example, incorporate a conventional line shaft encoder 112, which is operably connected to the primary line shaft 114 of the apparatus 20. In addition, a reference signal generator 116 is operably connected to the line shaft 114 to generate one reference pulse per each individual product section, which is intended to be derived from the composite fibrous web 12. The output from the reference generator 116 and the line shaft encoder 112 are directed to a programmable controller 118, such as a computer, through suitable signal conduits. The programmable controller 118 allows for the manual input of variable control parameters, such as through a conventional keyboard. The programmable controller 118, in turn, selectively controls the rotation of the rotatable drum 70 to provide the desired registration of the intermittent layer of particulate material 14 (FIGS. 1C and 1D) within the composite fibrous web 12. In a particular aspect of the invention, the programmable controller 118 may directly control an electric motor which rotates the shaft 80 of the rotatable drum 70. Alternatively, the programmable controller 118 may control the rotation of any of the other elements of the apparatus 20 which, in turn, controls the rotation of the rotatable drum 70. For example, the programmable controller 118 may control the rotation of the foraminous forming layer 90 which, in turn, controls the rotation of the rotatable drum 70.

In the illustrated embodiment, the line shaft encoder 112 may be a 63-P-MEF-2000-T-0-00GH device manufactured by Dynapar Corp. located in Gurnee, Ill. The encoder may, for example, be configured to generate 2000 pulses per revolution. The reference signal generator 116 may, for example, comprise a B15-G18-ANGX proximity switch manufactured by TURCH, a business located in Minneapolis, Minn. A suitable programmable controller 118 may, for example, comprise a device manufactured and designated as a PME 68-23 CPU by Radstone Technology, a company located in Pearl River, N.Y.

The various aspects of the apparatus and method of the invention may also include a mechanism for adding a bonding agent to the composite fibrous web 12 to further define the discrete layer of particulate material 14 (FIGS. 1A–1D). For example, a bonding agent may be sprayed onto the particulate material before the second fibrous layer 18 is formed on the layer of particulate material 14. Any bonding agent that provides the desired definition of the discrete layer of particulate material 14 may be used in the present invention. For example the bonding agent may include water or an adhesive such as a latex or hot melt adhesive. The bonding agent add-on rate may vary depending upon the desired composite fibrous web 12. For example, the bonding agent may be water which is added at a rate of from about 0 to about 20 weight percent based on the total weight of the particulate material 52 in the composite fibrous web 12.

The composite fibrous web of the different aspects of the present invention has the structural configuration of a composite of an airlaid fibrous material and an airlaid particulate material. As representatively illustrated in FIGS. 1A and 1B, the composite fibrous web 12 may include a layer of particulate material 14 disposed between a first fibrous layer 16 and a second fibrous layer 18. Alternatively, as representatively illustrated in FIGS. 1C and 1D, the composite fibrous web 12 may include an intermittent layer of particulate material 14 disposed between a first fibrous layer 16 and a second fibrous layer 18. Desirably, the layer of particulate material 14 is substantially isolated within a discrete layer and is substantially free of fibrous material 32. Moreover, the first fibrous layer 16 and second fibrous layer 18 can be substantially free of particulate material 52.

The composite fibrous web 12 of the different aspects of the present invention may contain variable weight percentages of particulate material based on the total weight of the composite fibrous web. For example, the composite fibrous web can contain 25–75 weight percent of the particulate material, and preferably includes about 30–60 weight percent of the particulate material based on the total weight of the composite fibrous web.

In the illustrated aspects of the invention, the second forming chamber 40 can be selectively configured and located within the first forming chamber 22, as representatively illustrated in FIGS. 2, and 4–5, to vary the weight percentages of the fibrous material present in the first and second fibrous layer based on the total weight of the fibrous material present in the composite fibrous web. For example, the first fibrous layer 16 (FIGS. 1A–1D) may contain from about 35 to about 65 weight percent of the fibrous material based on the total weight of the fibrous material present in the composite fibrous web and the second fibrous layer 18 (FIGS. 1A–1D) may contain from about 35 to about 65 weight percent of the fibrous material based on the total weight of fibrous material present in the composite fibrous web 12. Desirably, the first fibrous layer 16 contains from about 40 to about 60 weight percent of the fibrous material and the second fibrous layer 18 contains from about 40 to about 60 weight percent of the fibrous material based on the total weight of fibrous material present in the composite fibrous web 12.

Alternatively, the second forming chamber 40 can be located adjacent or near the end wall 26 or end wall 28 of the first forming chamber 22 such that the particulate material 52 is deposited directly on or near the surface of the foraminous forming layer 90 or on or near the top of the fibrous material 32 to form the composite fibrous web 12. For example, if the second forming chamber is located near the end wall 26, the first fibrous layer may contain from 0 to about 25 weight percent of the fibrous material based on the total weight of fibrous material present in the composite fibrous web 12. Alternatively, if the second forming chamber is located near the end wall 28, the first fibrous layer may contain from about 75 to 100 weight percent of the fibrous material based on the total weight of fibrous material present in the composite fibrous web 12. Thus, the z-directional placement of the layer of particulate material can be varied across the thickness of the composite fibrous web 12 by varying the position of the second forming chamber 40 within the first forming chamber 22.

The resultant composite fibrous web can include a distinctive, selectively varied distribution of particulate material along both the machine direction and the cross direction of the composite fibrous web. Moreover, the distribution of particulate material may also be varied along the z-direction or thickness of the composite fibrous web by varying the position of the second forming chamber within the first forming chamber. For example, the average weight percentage of particulate material can be nonuniformly distributed along the machine direction and the cross direction of the composite fibrous web. FIGS. 3A and 3B representatively illustrate different patterns for the forming grate of the present invention which may be used to provide varied distributions of particulate material within the composite fibrous web. FIGS. 6A, 6B and 7A–7D representatively illustrate several different configurations for the drum opening in the rotatable drum of the present invention which can also be used to provide varied distributions of particulate material within the composite fibrous web.

Thus, the present invention can advantageously provide a discrete layer of particulate material within a composite fibrous web. The present invention can also provide an intermittent, discrete layer of particulate material within a composite fibrous web wherein the layer of particulate material is located at spaced apart locations along the length of the composite fibrous web. The layer of particulate material may be located at the spaced apart locations along the length of the composite fibrous web without also locating a corresponding, greater (or smaller) proportion of the fibrous material at those spaced apart locations. Thus, the concentration of particulate material at a particular location may be configured to be substantially independent of the amount (e.g. basis weight) of fibrous material at that location. The present invention can also provide a layer of particulate material within a composite fibrous web wherein the layer of particulate material is configured in a selected pattern.

Alternatively, the apparatus and method of the different aspects of the present invention may utilize two or more secondary forming chambers located within the first forming chamber to provide multiple layers of particulate material. The multiple layers of particulate material may be configured in varying patterns, deposited intermittently or any combination thereof to provide the desired composite fibrous web.

Figure 9:
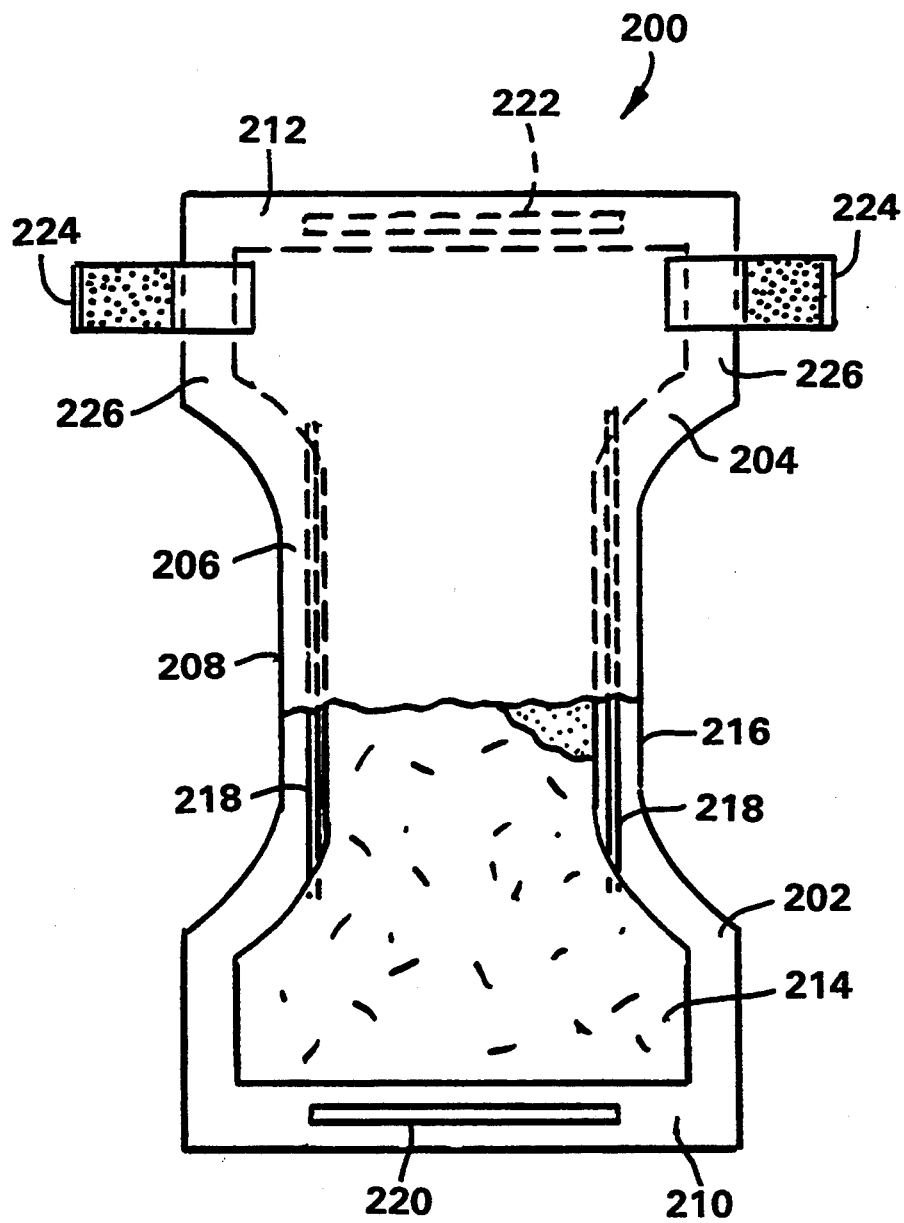
FIG. 9 representatively shows an absorbent article having an absorbent core which includes a composite fibrous web formed by the present invention.

An absorbent article, such as a disposable diaper, which uses the composite fibrous web of the present invention as an absorbent core is representatively illustrated in FIG. 9. The absorbent article 200 defines a front portion 202, a rear portion 204, and a crotch portion 206 connecting the front portion 202 and the rear portion 204. The absorbent article 200 includes a bodyside liner 210, an outer cover 212 and an absorbent core 214 located between the bodyside liner 210 and the outer cover 212. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 206 has opposite longitudinal side portions 208 which include a pair of elasticized, longitudinally-extending leg cuffs 216. The leg cuffs 216 are generally adapted to fit about the legs of a wearer in use and serve as a mechanical barrier to the lateral flow of body exudates. The leg cuffs 216 are elasticized by a pair of leg elastics 218. The absorbent article 200 further includes a front waist elastic 220 and a rear waist elastic 222. The rear portion 204 of the absorbent article 200 further includes a fastening means such as a pair of tape fasteners 224. The tape fasteners 224 are intended to hold the absorbent article 200 about the waist of the wearer when in use.

The bodyside liner 210 of the absorbent article 200, as representatively illustrated in FIG. 9, suitably presents a body-facing surface which is compliant, soft-feeling and nonirritating to the wearer's skin. Further, the bodyside liner 210 may be less hydrophilic than the absorbent core 214, to present a relatively dry surface to the wearer, and may be sufficiently porous to be liquid permeable, permitting liquid to readily penetrate through its thickness. A suitable bodyside liner 210 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 210 is suitably employed to help isolate the wearer's skin from liquids held in the absorbent core 214.

Various woven and nonwoven fabrics can be used for the bodyside liner 210. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 210 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The outer cover 212 of the absorbent article 200, as representatively illustrated in FIG. 9, may suitably be composed of a material which is either liquid permeable or liquid impermeable. It is generally preferred that the outer cover 212 be formed from a material which is substantially impermeable to liquids. For example, a typical outer cover can be manufactured from a thin plastic film or other flexible liquid-impermeable material. For example, the outer cover 212 may be formed from a polyethylene film having a thickness of from about 0.012 millimeter (0.5 mil) to about 0.051 millimeter (2.0 mils). If it is desired to present the outer cover 212 with a more clothlike feeling, the outer cover 212 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 212 may be formed of a woven or nonwoven fibrous web layer which has been totally or partially constructed or treated to impart a desired level of liquid impermeability to selected regions that are adjacent or proximate the absorbent core 214. Still further, the outer cover 212 may optionally be composed of a micro-porous "breathable" material which permits vapors to escape from the absorbent core 214 while still preventing liquid exudates from passing through the outer cover 212.

The absorbent core 214 of the absorbent article 200, as representatively illustrated in FIG. 9, may suitably comprise the composite fibrous web 12 of the different aspects of the present invention as representatively illustrated in FIGS. 1A–1D. The layer of particulate material 14 of the composite fibrous web 12 desirably includes a high absorbency material. As a general rule, the high absorbency material is present in the absorbent core 214 in an amount of from about 5 to about 100 weight percent based on total weight of the absorbent core to provide more effective performance. The absorbent core 214 may have any of a number of shapes. For example, the absorbent core may be rectangular, I-shaped or T-shaped. It is generally preferred that the absorbent core be narrower in the crotch portion 206 of the absorbent article 200 than in the front or rear portion, 202 or 204, respectively.

In particular aspects of the invention, the layer of particulate material of the composite fibrous web of the present invention may be configured in a pattern or intermittently deposited at spaced apart locations to improve the performance of the absorbent core. For example, the layer of particulate material may be deposited in discrete strips, as representatively illustrated in FIGS. 1A and 1B, to improve the wicking characteristics of the composite fibrous web. While not intending to be bound by any particular theory, it is believed that the improved wicking characteristics of the composite fibrous web result from the decreased occurrence of "gel blocking" which occurs with the use of high absorbency or superabsorbent materials as is well known to those skilled in the art.

In particular aspects of the invention, the apparatus and method of the present invention can be configured such that at least about 50 weight percent and not more than about 95 weight percent of the total amount of high absorbency particles are located in the front 50 percent of the overall length of the absorbent core 214. Preferably, about 55–85 weight percent and more preferably, about 60–85 weight percent of the total amount of high absorbency particles are located in the front 50 percent of the overall absorbent core length. Such weight percentages of high absorbency particles, however, may not be present in combination with corresponding, similar weight percentages of the total amount of fibrous material in the absorbent core 214. For example, the front 50 percent of the length of the absorbent core 214 may include 60–80 weight percent of the total amount of high absorbency material but only include 55 weight percent of the total amount of fibrous material. As another example, the front 50 percent of the absorbent core may include 60–80 weight percent of the total amount of high absorbency material, but only include 40–50 weight percent of the total amount of fibrous material.

In further aspects of the invention, relatively higher weight percentages of the particulate material can be selectively located at predetermined locations along the length of the absorbent core. For example, 50–60 weight percent of the total amount of fibrous material may be located in a front 45 percent of the absorbent core while 50–80 weight percent of the total amount of particulate material is located in a middle 30 percent of the absorbent core. Thus, the region having the maximum weight percentage of fibrous material can be offset lengthwise from the region having the maximum weight percentage of particulate material.

The outer cover 212 and bodyside liner 210 are generally adhered to one another so as to form a pocket in which the absorbent core 214 is located. Thus, the leg cuffs 216 are suitably formed by portions of the outer cover 212, and/or bodyside liner 210, which extend beyond the longitudinal sides of the absorbent core 214. Naturally, the leg cuffs 216 can also be formed from separate materials which are attached to the outer cover 212 and/or bodyside liner 210.

The leg cuffs 216, as representatively illustrated in FIG. 9, include leg elastics 218. Materials suitable for use in forming leg elastics 218 are known to those skilled in the art. Exemplary of such materials are strands or ribbons of a polymeric, elastomeric material which are adhered to the absorbent article 200 at the leg cuffs 216 while in a stretched position, or which are attached to the absorbent article while the article is pleated, such that elastic constrictive forces are imparted to the leg cuffs 216.

Similarly, waist elastics 220 and 222 and tape fasteners 224, as representatively illustrated in FIG. 9, are known to those skilled in the art.

A wide variety of diaper configurations, as well as training pant, incontinence garments and like configurations, are suitable for using the composite fibrous web of the present invention. Suitable diapers are described in greater detail in commonly assigned U.S. patent application Ser. No. 07/757,760 entitled "Thin Absorbent Article Having Rapid Uptake of Liquid" filed Sep. 11, 1991, in the name of Hansen et al, now abandoned.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. An apparatus for forming a discrete layer of particulate material within a composite fibrous web comprising:
   (a) a first forming chamber;
   (b) a supplying means for providing a flow of a selected fibrous material into said first forming chamber;
   (c) a second forming chamber which is selectively located within said first forming chamber to selectively divide said flow of said fibrous material;
   (d) a conveying means for transporting a particulate material into said second forming chamber;
   (e) a depositing means located within said second forming chamber for selectively dispensing said particulate material; and
   (f) a foraminous forming layer which is movably disposed within said first forming chamber and which is configured to receive said flow of said fibrous material and said dispensed particulate material;
   said foraminous forming layer being constructed to receive a formation of a first fibrous layer, to receive said dispensed particulate material on said first fibrous layer, and to receive a second fibrous layer formed on said particulate material, thereby forming said discrete layer of particulate material within said composite fibrous web.

2. The apparatus of claim 1 wherein said depositing means includes a forming grate which has at least one grate opening therethrough configured to dispense said particulate material on said first fibrous layer in a selected pattern.

3. The apparatus of claim 2 wherein said grate opening includes at least two channels configured to dispense said particulate material on said first fibrous layer in discrete strips along a length of said composite fibrous web.

4. The apparatus of claim 1 wherein said depositing means includes a rotatable drum which has an interior chamber therein and at least one drum opening therethrough.

5. The apparatus of claim 4 wherein said rotatable drum is configured to receive said particulate material in said interior chamber and intermittently dispense said particulate material through said drum opening as said rotatable drum rotates such that said particulate material is intermittently dispensed on said first fibrous layer at spaced apart locations along a length of said composite fibrous web.

6. The apparatus of claim 4 wherein said drum opening varies across a width and a circumferential length of said rotatable drum.

7. The apparatus of claim 6 wherein said drum opening is configured in an elliptical pattern.

8. The apparatus of claim 1 wherein said foraminous forming layer is a foraminous forming screen configured as an endless belt.

9. The apparatus of claim 1 wherein said foraminous forming layer is a foraminous forming screen configured on an outer circumferential surface of a forming drum.

10. The apparatus of claim 1, further comprising a vacuum means for drawing said fibrous material and said particulate material onto said foraminous forming layer.

11. The apparatus of claim 5, further comprising a phasing means for controlling a rotation of said rotatable drum to provide a desired registration between said spaced apart locations and a selected deposition region along a length of said composite fibrous web.

12. A method for forming a patterned, discrete layer of particulate material within a composite fibrous web, said method comprising the steps of:
(a) providing a flow of a selected fibrous material into a first forming chamber;
(b) providing a flow of a particulate material into a second forming chamber which is selectively located within said first forming chamber to selectively divide said flow of fibrous material; and
(c) depositing said fibrous material and said particulate material on a moving, foraminous forming layer located within said first forming chamber wherein, as said foraminous forming layer moves, a first fibrous layer is formed on said foraminous forming layer, said particulate material is deposited on said first fibrous layer in a selected pattern, and a second fibrous layer is formed on said particulate material thereby forming said patterned, discrete layer of particulate material within said composite fibrous web.

13. The method of claim 12 wherein said step of depositing said fibrous material includes the step of forming said first fibrous layer such that it contains of from about 35 to about 65 weight percent of said fibrous material based on a total weight of fibrous material present in said composite fibrous web.

14. The method of claim 12 wherein said step of providing said flow of said particulate material includes the step of providing said particulate material in an amount of from about 25 to about 75 weight percent based on a total weight of said composite fibrous web.

15. The method of claim 12 wherein said step of providing said flow of said particulate material includes the step of providing a high absorbency material.

16. The method of claim 12 wherein said step of depositing said fibrous material includes the step of maintaining said first fibrous layer and said second fibrous layer substantially free of said particulate material.

17. The method of claim 12 wherein said step of depositing said particulate material includes the step of maintaining said patterned, discrete layer of particulate material substantially free of said fibrous material.

18. The method of claim 12 wherein said step of depositing includes the step of providing a forming grate which is located within said second forming chamber and has at least one grate opening therethrough such that said particulate material is selectively deposited on said first fibrous layer in said selected pattern.

19. The method of claim 18 wherein said step of providing said forming grate includes the step of providing at least two channels in said grate to provide said grate opening such that said particulate material is deposited on said first fibrous layer in discrete strips along a length of said composite fibrous web.

20. The method of claim 12, further comprising the step of providing a vacuum to draw said fibrous material and said particulate material onto said foraminous forming layer.

21. The method of claim 12, further comprising the step of adding a bonding agent to said composite fibrous web to further define said patterned, discrete layer of particulate material.

22. A method for forming an intermittent, discrete layer of particulate material within a composite fibrous web, said method comprising the steps of:
(a) providing a flow of a selected fibrous material into a first forming chamber;
(b) providing a flow of a particulate material into a second forming chamber which is selectively located within said first forming chamber to selectively divide said flow of said fibrous material into a first portion and a second portion;
(c) depositing said first portion of said fibrous material on a moving, foraminous forming layer located within said first forming chamber to provide a first fibrous layer;
(d) intermittently depositing said particulate material on said first fibrous layer; and
(e) depositing said second portion of said fibrous material on said particulate material to provide a second fibrous layer thereby forming said intermittent, discrete layer of particulate material within said composite fibrous web.

23. The method of claim 22 wherein said step of intermittently depositing said particulate material includes the step of providing a rotatable drum which is located within said second forming chamber and has an interior chamber therein and at least one drum opening therethrough, said drum receiving said particulate material in said interior chamber and selectively dispensing said particulate material through said drum opening as said drum rotates such that said particulate material is intermittently deposited at spaced apart locations along a length of said composite fibrous web.

24. The method of claim 23 wherein said step of providing a rotatable drum includes the step of providing said drum opening such that said particulate material is intermittently deposited within a center portion of said composite fibrous web which is located between two outer portions of said composite fibrous web, said outer portions of said composite fibrous web being substantially free of said particulate material.

25. The method of claim 23 wherein said step of providing said rotatable drum includes the step of providing said drum opening in a selected pattern such that said particulate material is intermittently deposited on said first fibrous layer in a patterned configuration.

26. The method of claim 22, further comprising the step of providing a vacuum to draw said fibrous material and said particulate material onto said foraminous forming layer.

27. The method of claim 22, further comprising the step of adding a bonding agent to said composite fibrous web to further define said intermittent, discrete layer of particulate material.

* * * * *